United States Patent [19]
Nicholas et al.

[11] Patent Number: 5,859,696
[45] Date of Patent: Jan. 12, 1999

[54] REFRACTOMETER FOR DISTINGUISHING SUGAR-SWEETENED BEVERAGES FROM ARTIFICIALLY-SWEETENED ONES

[76] Inventors: Paul Nicholas; Rhonda Nicholas, both of 640 S. Griffith Park Dr., Burbank, Calif. 91506

[21] Appl. No.: 984,908

[22] Filed: Dec. 4, 1997

[51] Int. Cl.⁶ .................................................. G01N 21/41
[52] U.S. Cl. .......................................... 356/128; 356/135
[58] Field of Search ............................ 356/128, 135–137

[56] References Cited

U.S. PATENT DOCUMENTS

| | | | |
|---|---|---|---|
| 4,650,323 | 3/1987 | Nakagawa | 356/135 |
| 4,890,916 | 1/1990 | Rainer | 356/135 |
| 5,355,211 | 10/1994 | Thompson et al. | 356/135 |

*Primary Examiner*—Frank G. Font
*Assistant Examiner*—Amanda Merlino
*Attorney, Agent, or Firm*—Edgar W. Averill, Jr.

[57] ABSTRACT

A low-cost refractometer for determining whether or not a beverage has been sweetened with sugar. The refractometer has an elongated transparent body with a prism at one end and either an eye piece or a light source at the other end. A drop of the beverage to be tested is put on the face of the prism and a diffuser is closed over it to spread the liquid into a thin sheet and to diffuse the light entering the prism face. The user looks through the eye piece at the remote end and because of a light block, light only shows through at the eye piece if there is sugar in the drink. Alternatively, a light may be directed at the eye piece end and if light is visible through the diffuser, the sample has sugar and if there is no light showing at the diffuser, the sample is essentially sugar-free.

16 Claims, 7 Drawing Sheets

REFRACTOMETER FOR DISTINGUISHING SUGAR-SWEETENED BEVERAGES FROM ARTIFICIALLY-SWEETENED ONES

BACKGROUND OF THE INVENTION

The field of the invention is optical instruments and the invention relates more particularly to refractometers.

It is often important to know whether a diet soda ordered at a restaurant is in fact a diet soda or instead is a sugar-sweetened beverage. This fact can be important to diabetics and other persons who are concerned about possible ill health effects from artificially sweetened beverages. Furthermore, dieters are concerned about the caloric content of sugar-sweetened beverages.

Commercially available refractometers are quite costly but have been known and are in common use by vintners and fruit growers to determine the sugar content of the fruit. This determines whether or not the fruit is ready for harvest. They are also used by beverage makers for quality control.

Typical refractometers have, in addition to their cost, the ability to determine quantitatively the sugar level in a sample. One such refractometer is shown in U.S. Pat. No. 1,522,639. A folding casing is pivoted over a pair of prisms A1 and A2. Internal optics provide an adjustment. The device is adjustable by turning knob G1 and a line of light is visible through lens D2 which permits the user to determine with accuracy the refractive index of the liquid to be tested. Needless to say, the device is expensive.

A somewhat less expensive refractometer is shown in U.S. Pat. No. 2,383,347 where a prism has three exit faces each of which has an objective lens 15, 16 and 17, to project the light beams passing through the three exit faces of prism 3. The refractometer is capable of determining the refractive index of a wide range of liquid samples.

A refractometer with an improved line of demarcation between the light field and the dark field is shown in U.S. Pat. No. 2,972,926. This patent also shows a refractometer illuminated by a light bulb. Another illuminator is shown in a refractometer in U.S. Pat. No. 4,890,916.

Because the refractive index of a sample varies with temperature, refractometers are often equipped with temperature compensating mechanisms. They have adjustable focus eye pieces to provide a sharp image of the scale Commercial devices are fairly bulky and generally cost several hundred dollars.

The sugar-sweetened versions of most soft drinks contain 12% sugar by weight as they come from the bottle or from a properly adjusted drink fountain. These soft drinks vary in sugar level to as low as 6% after dilution by melted ice. At this concentration, the beverage is so watery most people find it undrinkable. The diet versions contain very nearly 0% sugar by weight and in fact, are virtually indistinguishable by refractometer measurement from tap water.

The inventor wished to provide a device which could be easily afforded by persons needing to know whether a drink is sugar-sweetened or not. People with phenyl ketonuria (PKU) are unable to properly metabolize phenylalanine and must avoid aspartame, a common artificial sweetener. Other people experience nervous system disturbances when they drink beverages containing aspartame and may wish to avoid diet soft drinks. Many people are wary of the possible long term health effect of consuming artificial sweeteners and may want to avoid them to reduce their risk of cancer and other illnesses. Dieters also are concerned about their caloric intake.

Various alternative test methods are available for determining the presence of sugar. One such test is a urine test tape which when contacted with a sugar-sweetened substance changes color. There are two disadvantages of this test. First, it is relatively expensive. Secondly, the strips have a relatively short life span since the color indicator is somewhat unstable. Also, one ends up with a wet strip which must be disposed of.

BRIEF SUMMARY OF THE INVENTION

It is an object of the present invention to provide a low cost device for determining whether or not sugar is present in a beverage.

The present invention is for a refractometer for distinguishing sugar-sweetened beverages from sugar-free beverages. The refractometer has an elongated transparent member having a prism end and a remote end and a central body with a central axis. The transparent member is covered or painted to prevent light from entering along its central body and a prism is formed at the prism end including a prism face on the upper surface. A diffuser may be moved into one position where the prism face is exposed for placement of a drop of beverage and to a second position where it is closely adjacent the prism face. The diffuser acts to not only spread the sample but also to diffuse the light entering the prism face to provide light entry in many planes so that there will not be a false reading. A light barrier is positioned in the central body of the elongated transparent member which blocks light entering the transparent member below the light barrier. The light barrier in the prism is selected so that refractive indices similar to water will cause the light to be blocked whereas refractive indices of sugar-sweetened substances cause a further refraction of the light rays so that the user observes light through the eye piece when such refractive index is present. Alternatively, a light may be placed at the eye piece or remote end of the transparent body and the device viewed from the prism end. Once again, the sample is placed on the prism surface beneath the diffuser and spread out by the diffuser. When the light is turned on, if the sample contains sugar, light will be visible at the prism end, and if it does not contain sugar, it will not be visible from the prism end. The refractometer may be made to include a light source such as LED and batteries so that the device can be operated in dimly lit restaurants or at night. The device is small, inexpensive and very easy to use.

DESCRIPTION OF THE PREFERRED EMBODIMENTS

Figure 1:
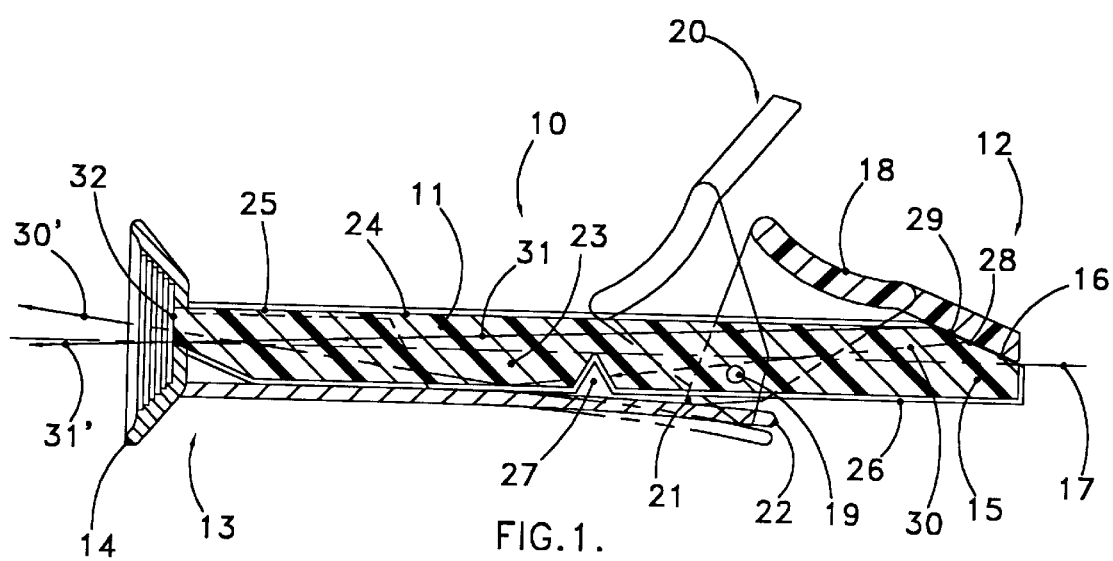
FIG. 1 is a cross-sectional side view of a first embodiment of the refractometer of the present invention.

The refractometer of the present invention is shown in cross-sectional side view in FIG. 1 and indicated generally by reference character 10. The body of the refractometer 10 is an elongated transparent member 11 which has a prism end 12 and a remote end 13. Remote end 13 in FIG. 1 includes an eye piece 14. Prism end 12 includes a prism 15 having a prism face 16.

Figure 6:
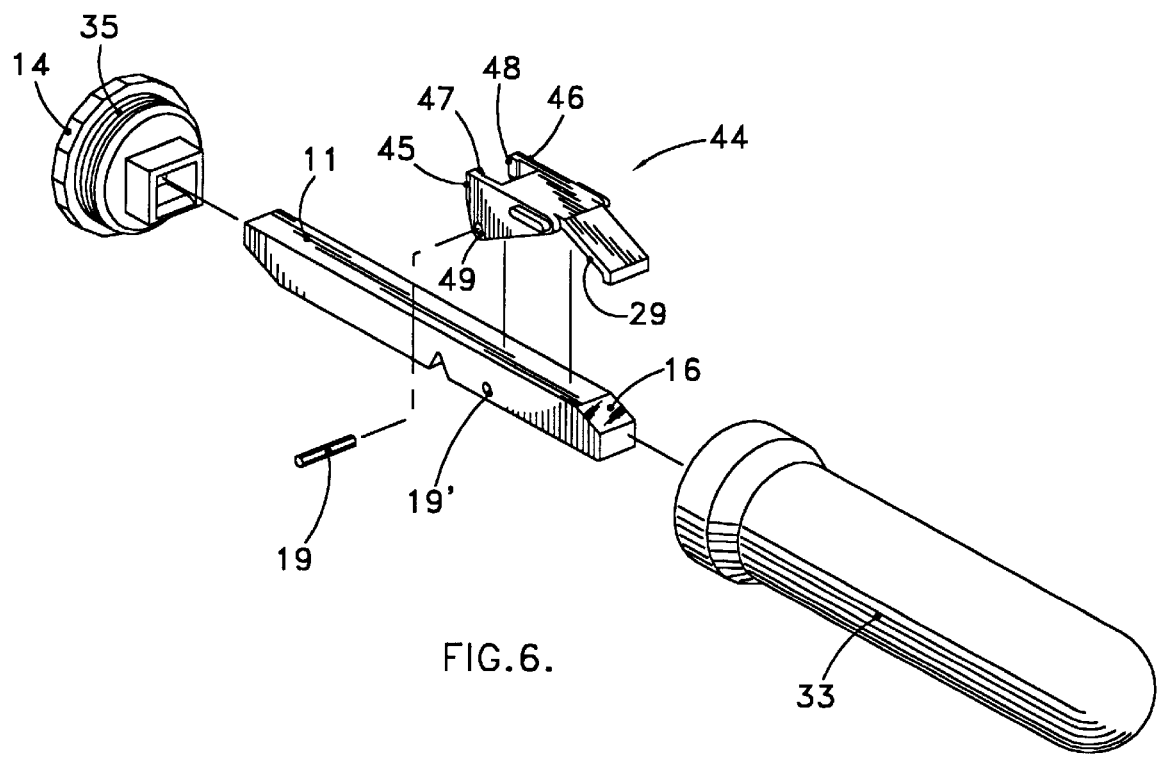
FIG. 6 is an exploded perspective view showing an alternate embodiment of the diffuser of the refractometer of FIG. 1.
Figure 7:
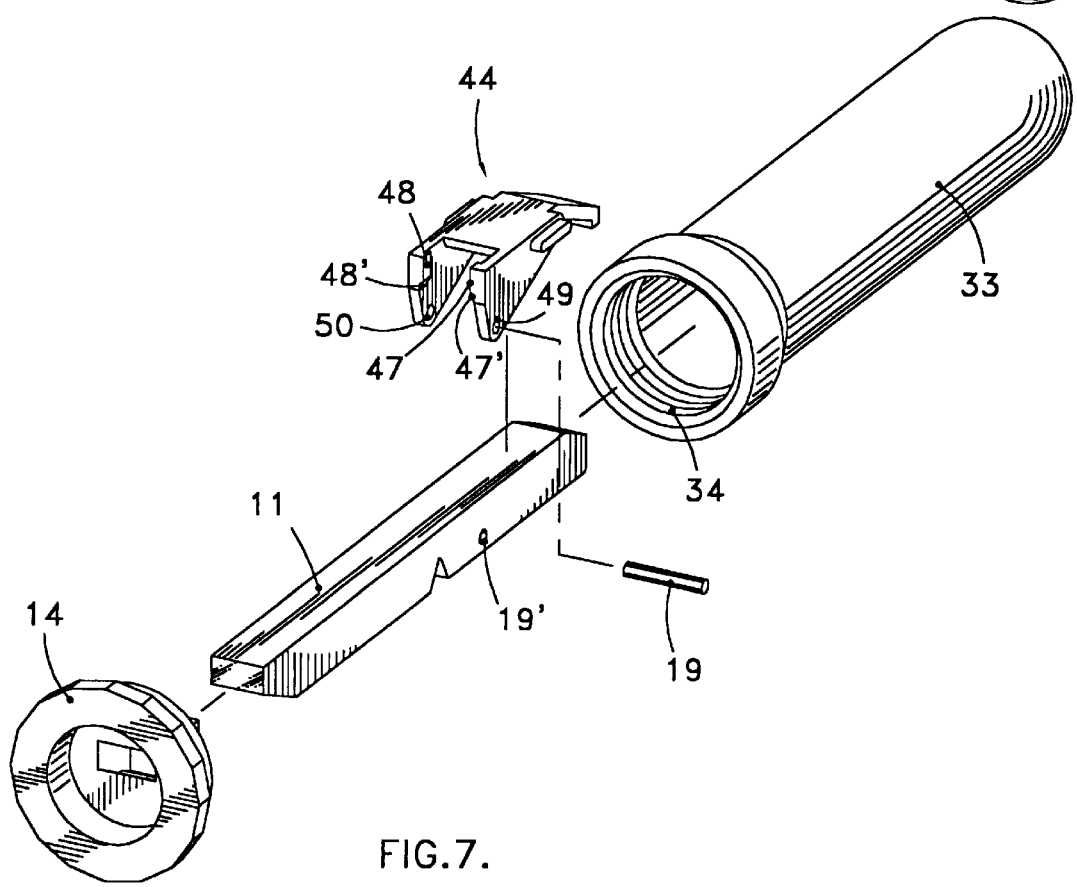
FIG. 7 is an exploded perspective view of the refractometer of FIG. 6.

The elongated transparent member 11 has a central axis 17 and is fabricated preferably from a polymer having excellent light-conducting characteristics such as the acrylic polymer sold under the trademark Lucite. A diffuser 18 is hinged by a pin 19 which extends through elongated transparent member 11 and permits the diffuser to go from its prism abutting position shown in solid lines in FIG. 1 to an open position indicated by reference character 20 in FIG. 1. Preferably the diffuser has a cam surface 21 which holds the diffuser in a bias closed position by contact with spring 22. When the diffuser is opened it is held in an open position by contact with the cam surface and spring 22. An alternate configuration of diffuser is shown in FIGS. 6 and 7 and indicated by reference character 44. Diffuser 44 has a pair of arms 47 and 48 extending rearwardly from the diffuser. These arms extend downwardly to openings 49 and 50. Pin 19 passes through openings 49 and 50 and through opening 19' which passes through elongated transparent member 11. A pair of cams 47 and 48 are formed on the inner surface of arms 45 and 46. When diffuser 44 is pivoted to an open position in phantom view in FIG. 1 and indicated by reference character 20, cams 47 and 48 press against the elongated body 11 and move arms 45 and 46 outwardly and hold the diffuser 44 in an open position. Then as diffuser 44 is moved to an almost closed position, beveled portions 47' and 48' abut the sides of body 11 and bias the prism mating face 29 against prism face 16.

The elongated transparent member 11 has a central body 23 which has an outer surface 24 which is coated with an opaque coating which may be either paint or a thin metal cover. The central body has an upper surface 25 and a lower surface 26. A light barrier or notch 27 is formed in the lower surface 26 and operates to block light rays so that no light is seen if a sugar-free sample is placed on prism face 16. For instance, assume that a sample 28 has been placed on prism face 16 when the diffuser is in an open position shown in phantom lines in FIG. 1. The drop of sample is then spread out into a thin sheet by the closing of the diffuser which has a prism mating face 29 which is flat and causes the sample to be spread into a thin film on prism face 16. Two rays of light are shown in FIG. 1. One ray 30 abuts the light barrier 27 and is not visible through the eye piece. If the light barrier were not present, the light could be reflected as shown by ray 30' and might give a false reading. A light ray passing through a sugar-containing substance is indicated by reference character 31 and can be seen to be visible at 31' through eye piece 14 which includes a viewing window 32.

Figure 2:
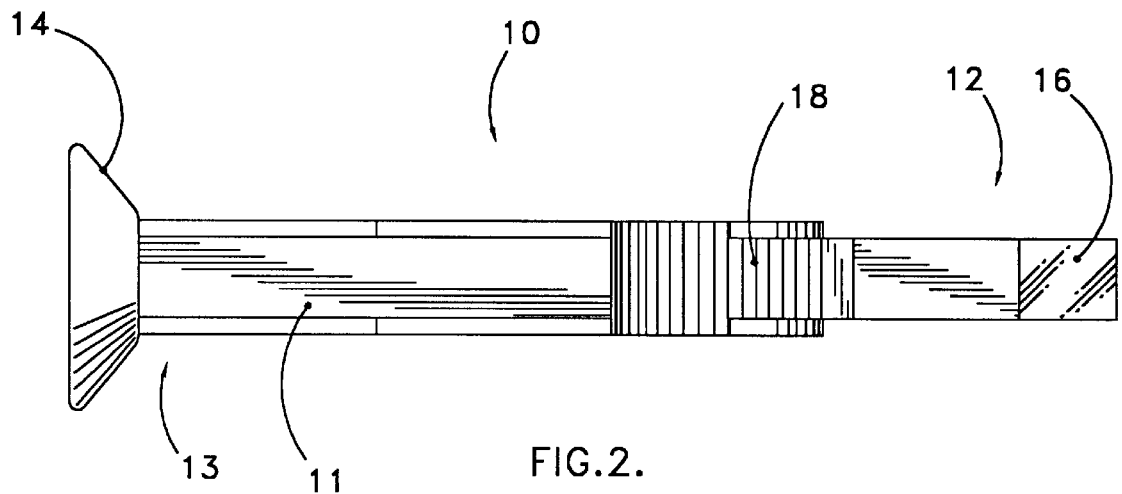
FIG. 2 is a top view thereof.

The refractometer can be seen to be capable of low cost manufacture and is shown in top view in FIG. 2. The diffuser is shown in a raised position in FIG. 2 so that the prism face 16 is exposed for contact with a drop of the beverage to be tested.

Figure 3:
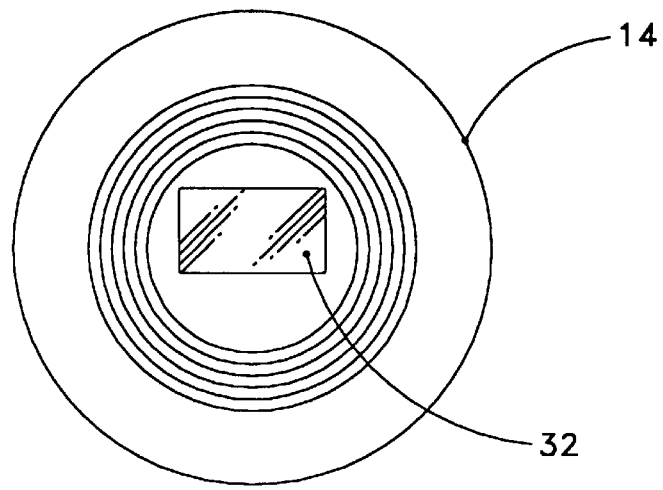
FIG. 3 is a left side view thereof.

When one looks through the viewing window 32 a rectangular image is presented which is either dark or light depending on whether or not the sample contains sugar. As a result, the user needs merely to lift the diffuser which is held up by the interaction of the cam face and the spring and place a drop on prism face 16. The diffuser is then closed and the user looks through eye piece 14. If the viewing window is light the sample has sugar. If it is dark the sample does not have sugar. As can be seen from the drawings of FIGS. 1, 2 and 3 the device of the present invention can be economically fabricated and easily used.

Figure 4:
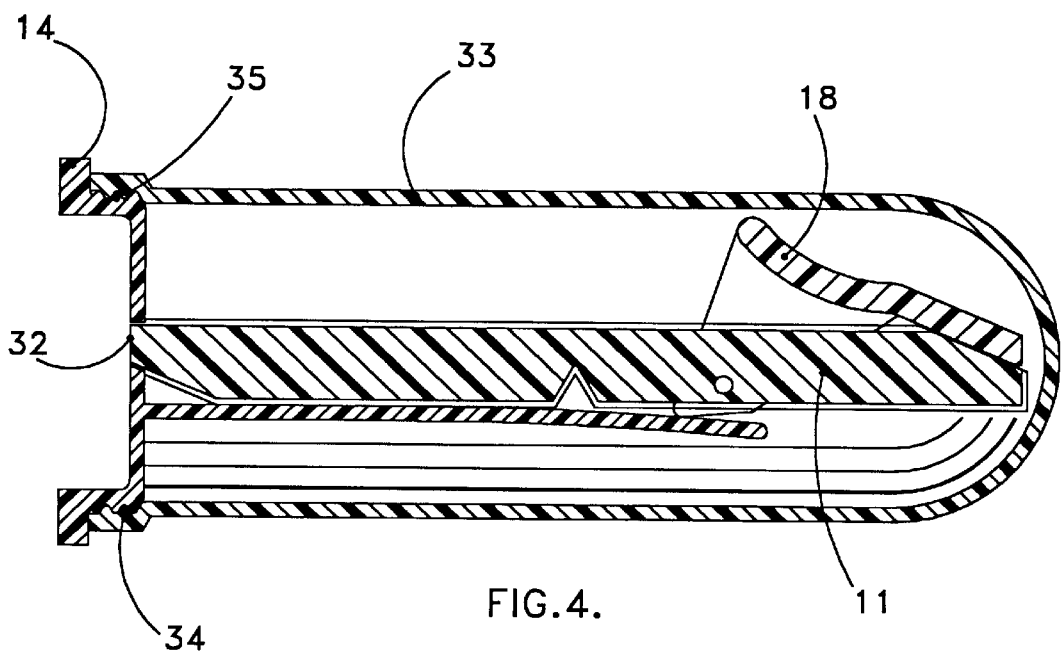
FIG. 4 is a cross-sectional side view of a covered version thereof.

The device may be readily encased by case 33 shown in FIG. 4. Case 33 has a female thread 34 which screws onto a male thread 35 on eye piece 14.

Figure 5:
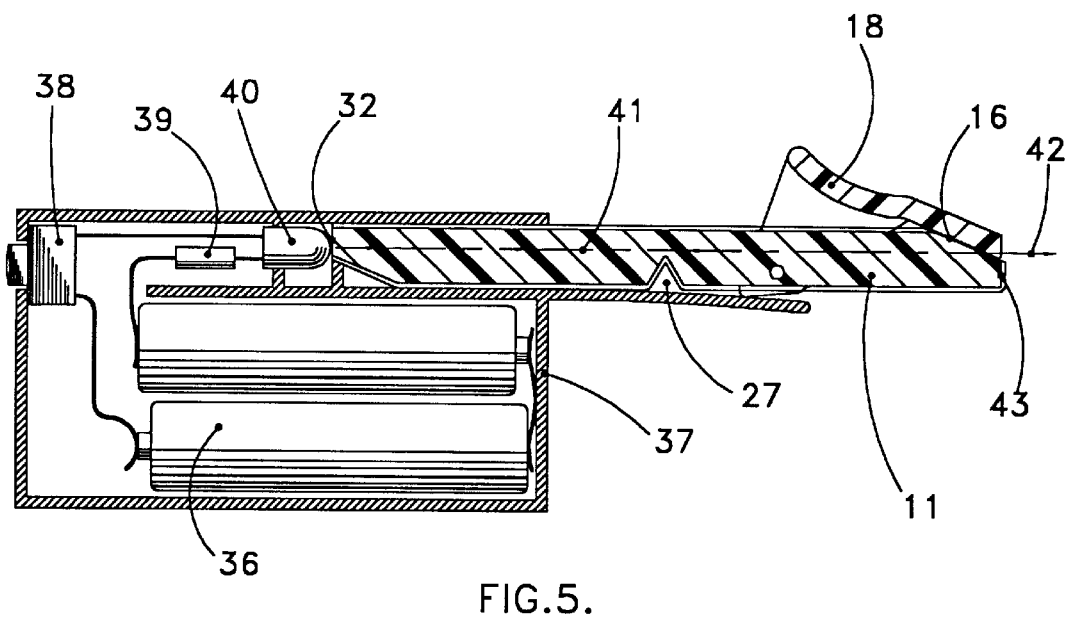
FIG. 5 is a cross-sectional side view of a battery operated version thereof.

While the device of the FIGS. 1–4 utilize ambient light entering through the prism, it is also possible that the device be reversed and light passed through the viewing window 32 and viewed from the prism face end of the device. Such a device is shown in FIG. 5 where batteries 36 are shown held in a frame 37. These batteries are wired through a switch 38, a current limiting resistor 39 to a light source such as LED 40. Thus, when switch 38 is turned on, a light ray 41 is partially blocked by light barrier 27. If the sample is a sugar-containing sample, the light ray emerges as indicated at reference character 42. Instead, if the sample contains no sugar, the light ray is refracted into the closed end 43 and thus, not visible through diffuser 18.

As a result the device of FIG. 5 can be used in dimly lit places or at night where there is not sufficient ambient light to permit a determination to be made in the way possible with the device of FIGS. 1–4.

The prism face is of course polished. The angle of the prism face is chosen to be slightly less than the angle for total internal reflection when the prism face is interfaced with water. Therefore, light cannot enter the prism face and travel lengthwise through the device unless the prism face is in contact with the medium whose refractive index is higher than that of water which is approximately 1.33. The diffuser is preferably made of a material such as textured clear plastic and acts to scatter incoming light so that the prism face is bathed in light which effectively comes from all directions. This assures that some light is traveling tangential to the prism face and can therefore enter the device when the refractive index of the sample is sufficiently high.

Figure 8:
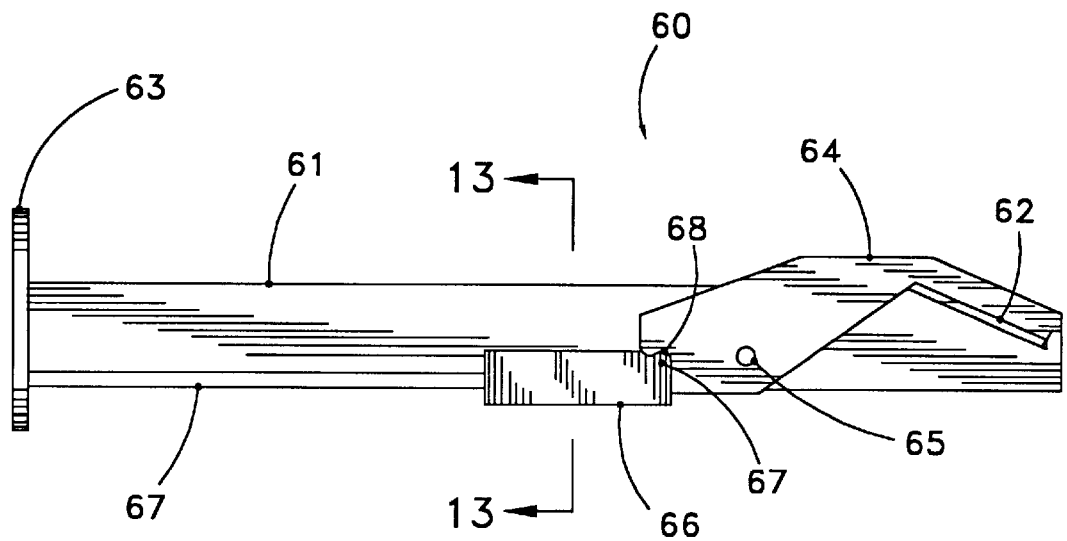
FIG. 8 is a side view of an alternate configuration of the refractometer of the present invention.
Figure 9:
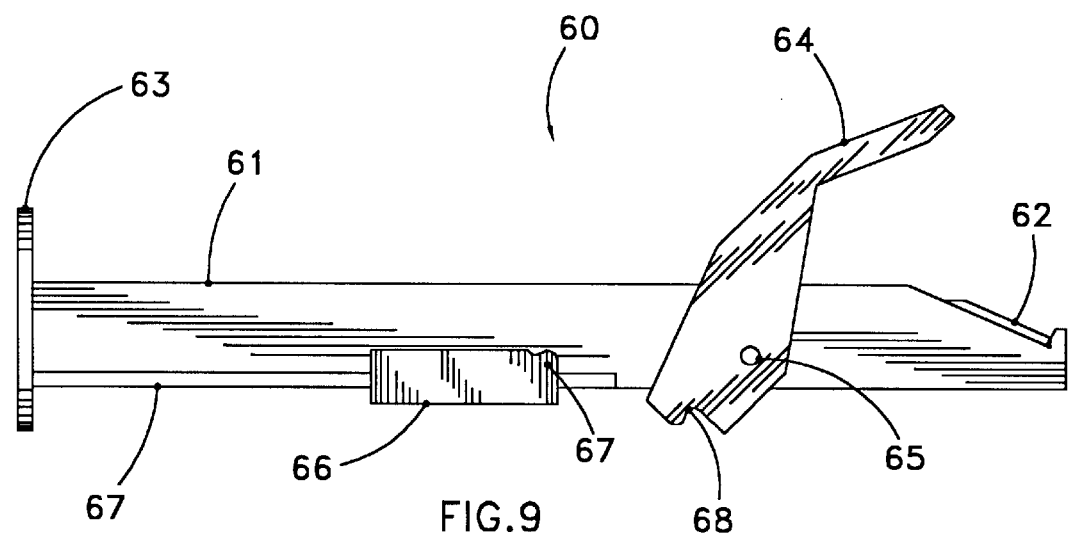
FIG. 9 is a side view of the refractometer of FIG. 8 showing the diffuser in an open position.

An economical embodiment of the refractometer is shown in FIGS. 8, 9, 10, 11, 12 and 13 and indicated generally by reference character 60. Refractometer 60 has a body 61 with a prism 62 at a prism end and an eye piece 63 at an eye piece end. A diffuser 64 is hingedly affixed at hinge 65 to body 61 and can move from a closed position shown in FIG. 8 to the open position shown in FIG. 9. A lock slide 66 slides along a track 67 shown best in cross-sectional view in FIG. 13. Lock slide 66 has a tab 67 which may be slid under a recess 68 in diffuser 64 to hold the diffuser in a closed position as shown in FIG. 8. The lock slide 66 may be moved toward eye piece 63 to permit the diffuser 64 to be open as shown in FIG. 9.

Figure 10:
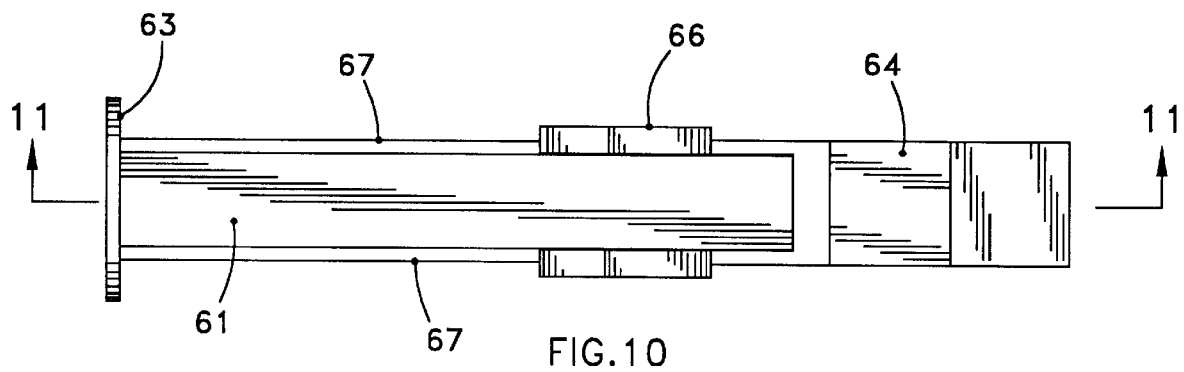
FIG. 10 is a top view of the diffuser of FIG. 8.
Figure 11:
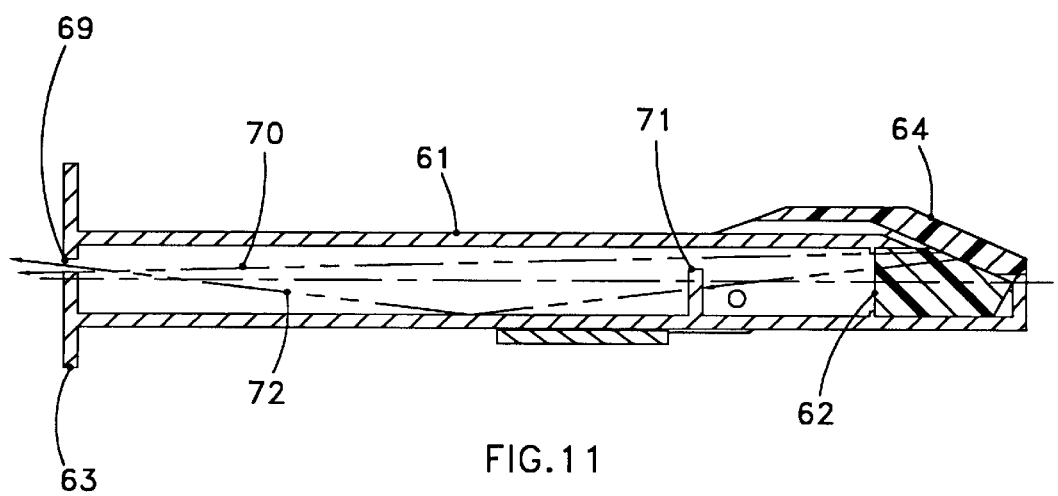
FIG. 11 is a cross-sectional side view of the diffuser of FIG. 8.
Figure 12:
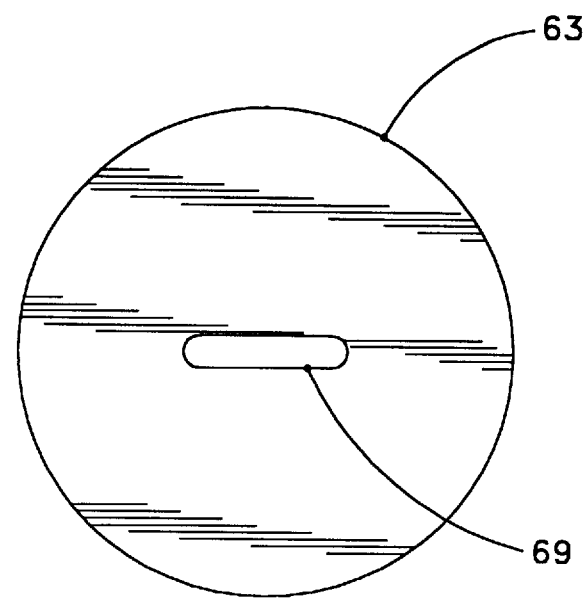
FIG. 12 is a rear view from the eye piece of the diffuser of FIG. 8.

The device is shown in top view in FIG. 10 where the track 67 can be seen to extend from both sides of body 61. The hinged diffuser 64 is shown in top view. A cross-sectional view taken along line 11—11 of FIG. 10 is shown in FIG. 11. A viewing slot 69 (also shown in FIG. 12) is formed in eye piece 63. The diffuser 64 is shown closed on prism 62 and transmitted light rays are indicated by reference character 70. An anti-reflection baffle 71 blocks light rays such as that indicated by reference character 72 and permits only rays indicating the presence of sugar to pass to the viewing slot 69. It can be seen that prism 62 is relatively short since the center of body 61 is hollow and permits the passage of light rays.

Figure 13:
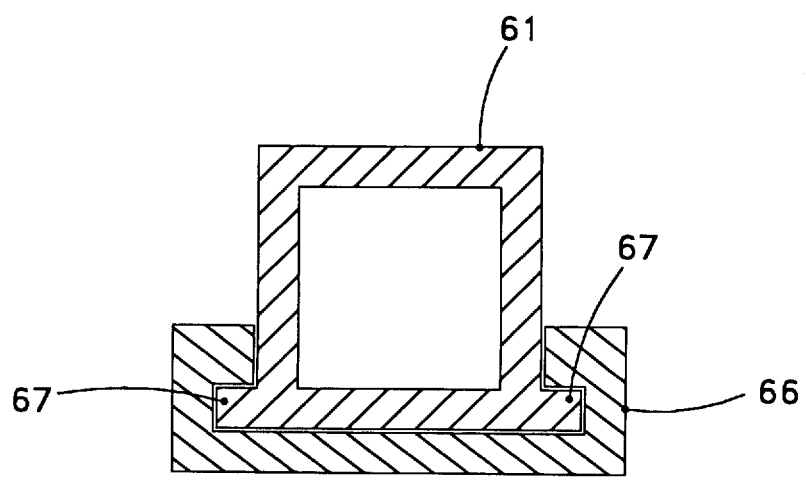
FIG. 13 is a cross-sectional view taken along line 13—13 of FIG. 8.

Lastly, in FIG. 13 the lock slide is shown to be captured by the track 67 to lock the diffuser in a closed configuration. The result is a refractometer of unusually economical configuration and yet highly accurate.

If the light barrier is eliminated, a possible problem exists in the reflection of light from the inner surface of the coated elongated body. The light barrier prevents this false reading possibility. Other blocking means could be devised to take the place of the light barrier, however, the light barrier is the preferred construction because of its low cost and effectiveness.

The result is a surprisingly effective, easy-to-use and low cost device which provides a degree of comfort to those to whom the presence of sugar or artificial sweetener is important.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

We claim:

1. A refractometer for distinguishing sugar-sweetened beverages from sugar-free beverages comprising:

an elongated transparent member having a prism end, a remote end, a central body having a central axis, an outer surface an upper surface, a lower surface, and means for preventing light from entering into said central body through said outer surface, said prism end including a prism face on said upper surface;

a diffuser having a prism-mating face movably placeable so that its prism-mating face may be moved into a mating position against said prism face and into a position removed from said prism face exposing the prism face;

a light barrier positioned in said central body along said lower surface whereby when a sample of sugar sweetened beverage is placed against said prism face and said diffuser is moved into a mating position thereby spreading said sample of sugar-sweetened beverage between said prism-mating face and said prism face and light enters one of said prism end and said remote end, light may be seen from the other of said ends but when a sample of sugar-free beverage is placed against said prism face and said diffuser is moved into a mating position thereby spreading said sample of sugar-free beverage between said prism-mating face and said prism face and light enters one of said prism end and said remote end, light may not be seen from the other of said ends thereby informing the user whether or not sugar is present.

2. The refractometer of claim 1 wherein light enters said prism end and said remote end further includes an eyepiece.

3. The refractometer of claim 1 wherein said elongated transparent member is held by as frame and wherein said light enters said remote end and said light is emitted from a light-emitting source held by said frame.

4. The refractometer of claim 3 wherein said light-emitting source is energized by at least one battery held by said frame.

5. The refractometer of claim 1 wherein said diffuser is hingedly affixed to said elongated transparent member.

6. The refractometer of claim 5 wherein said diffuser is fabricated from a polymer with a textured surface.

7. The refractometer of claim 5 wherein said diffuser is hingedly affixed by at least one hinge pin adjacent said elongated transparent body and said at least one hinge pin is held by at least one tab affixed to said prism mating face at one end and to said at least one hinge pin at another end and said tab includes a cam surface separated from said at least one hinge pin, said cam surface shaped to abut a biased cam-contacting arm and further shaped to hold said prism-mating face adjacent said prism face in a biased manner in a first position and, in a second position, to hold said prism-mating face away from said prism face.

8. The refractometer of claim 5 wherein said diffuser is formed with two downwardly depending arms which support a pin which is supported by said elongated transparent member and wherein said downwardly depending arms each have a cam formed thereon which cam includes a beveled portion, each cam abutting said elongated transparent member as said diffuser is hinged upwardly and each beveled portion being positioned so that it contacts said elongated transparent member when said diffuser is moved into said mating position, thereby biasing said diffuser into a biased contact with said prism face.

9. The refractometer of claim 1 wherein said light barrier is a notch formed in the lower surface of said elongated transparent member.

10. The refractometer of claim 2 wherein said eyepiece further includes an outwardly extending flange and said flange includes means for attachment of a case surrounding and protecting said prism, diffuser and elongated transparent member of said refractometer.

11. A process of determining whether or not a beverage is sugar free or sugar containing using a refractometer having a prism and prism face at one end and an eyepiece with a viewing port at the other end and a diffuser movably positionable into a prism-contacting position and a prism-separated position, and a light barrier positioned between said prism face and said eyepiece said process comprising:

moving said diffuser into a prism-separated position;
placing a drop of said beverage on said prism face;
moving said diffuser into a prism-contacting position thereby spreading said drop into a thin layer;
exposing said diffuser to a light source; and
viewing through said viewing port to determine whether or not light is present through said viewing port.

12. A process of determining whether or not a beverage is sugar free or sugar containing using a refractometer having a prism and prism face at one end and a light source at the other end and a diffuser movably positionable into a prism-contacting position and a prism-separated position and a light barrier positioned between said prism face and said eyepiece, said process comprising:

moving said diffuser into a prism-separated position;
placing a drop of said beverage on said prism face;
moving said diffuser into a prism-contacting position thereby spreading said drop into a thin layer;
energizing said light source; and
viewing at said prism face to determine whether or not light is present at said prism face.

13. A battery operated refractometer for determining whether or not a beverage contains sugar or not, said refractometer comprising:

a frame;
a transparent elongated member having a central axis, a prism end, a remote end and an elongated body protected from entrance by external light, said elongated member having an upper surface and a lower surface and a prism formed along said upper surface, a light barrier extending upwardly from said lower surface said prism having a prism face;

a light source held by said frame adjacent said remote end;

means for energizing said light source to emit light into said remote end; and a diffuser having a prism-mating face and positionable in a first position where said prism-mating face is removed from said prism face and a second position wherein said prism-mating face is adjacent said prism face.

14. A refractometer for determining whether or not a sample of liquid contains sugar or not comprising:

an elongated transparent member having a central body having a prism end, a viewing end, an external surface having an upper surface, a lower surface and a light barrier in said central body of said elongated transparent member;

a prism formed in said elongated transparent member at said prism end, said prism having a prism face;

an eyepiece at said viewing end, said eyepiece having a viewing port; and a diffuser having a prism-mating face and positionable in a first position where said prism-mating face is removed from said prism face and a second position wherein said prism-mating face is adjacent said prism face.

15. The refractometer of claim 14 wherein said diffuser is pivotally held to said elongated transparent member by at least one tab and said tab includes a cam member which is shaped to contact a biased arm to retain said diffuser in said first or said second position.

16. The refractometer of claim 14 wherein said light barrier is a notch formed from said lower surface of said external surface and extending about half way through said elongated transparent member.

* * * * *